United States Patent [19]

Koda et al.

[11] Patent Number: 5,480,905

[45] Date of Patent: Jan. 2, 1996

[54] BENZODIOXANE DERIVATIVES

[75] Inventors: Akira Koda; Tatsuo Miyauchi; Yoshitake Kanbe; Hirokazu Hamada, all of Shizuoka, Japan

[73] Assignee: Chugai Seiyaku Kabushiki Kaisha, Tokyo, Japan

[21] Appl. No.: 369,924

[22] Filed: Jan. 6, 1995

Related U.S. Application Data

[63] Continuation of Ser. No. 75,490, filed as PCT/JP92/01366, Oct. 21, 1992, abandoned.

[30] Foreign Application Priority Data

Oct. 22, 1991 [JP] Japan .................................. 3-274036
Apr. 27, 1992 [JP] Japan .................................. 4-107570
Oct. 16, 1992 [JP] Japan .................................. 4-278776

[51] Int. Cl.$^6$ ...................... A61K 31/335; C07D 319/16
[52] U.S. Cl. .................... 514/452; 514/456; 549/366; 549/362; 549/358; 549/357; 549/356
[58] Field of Search .................... 514/452, 456; 549/366, 362, 358, 357, 356

[56] References Cited

U.S. PATENT DOCUMENTS

5,010,078  4/1991  Abou-Gharbia et al. ............. 514/252
5,036,070  7/1991  Abou-Ghariba ..................... 514/252
5,126,367  6/1992  Stack et al. ....................... 549/366

FOREIGN PATENT DOCUMENTS

61-246180  11/1986  Japan .
215059  1/1990  Japan .

OTHER PUBLICATIONS

Jolicoeur et al, Pharmacol. Biochem & Behavior, 9, 845–847, 1978.
Riley, Physiology Psychology, 6(14), 488–492, 1978.
Jolicoeur et al, Pharmacol. Biochem & Behavior, 12, 613–617, 1980.
Concannon et al, Pharmacol. Biochem & Behavior, 13, 761–764, 1980.
Roache et al, Pharmacol. Biochem & Behavior, 25, 431–437, 1986.
Ervin et al, Drug Dev. Res. 11:87–95, 1987.
Ervin et al, J. Pharmac. & Eap. Ther. 245, No. 1, 137–146, 1988.

*Primary Examiner*—Shailendra Kumar
*Attorney, Agent, or Firm*—Birch, Stewart, Kolasch & Birch

[57] ABSTRACT

Compounds represented by the general formula (I):

$$R_1-\overset{O}{\underset{\|}{C}}-\underset{H}{N}-(CH_2)_n-\underset{|}{\overset{R_2}{N}}-CH_2-R_3 \qquad (I)$$

(where $R_1$ is an admantyl group; $R_2$ is a hydrogen atom, a lower alkyl group, a lower alkenyl group or an aralkyl group; $R_3$ is a 1,4-benzodioxane ring that may optionally have 1–4 substituents selected from among a lower alkyl group, a lower alkoxy group, a halogen atom, an amino group, a hydroxyl group and a lower alkylcarbonyl group; n is an integer of 1–4) or a salt thereof. These compounds have both antianxiety and antidepressant actions and yet they cause less side effects. Therefore, they can be used as excellent drugs that are highly effective in the prevention and treatment of various diseases such as neurosis. psychosomatic diseases, autonomic imbalance and depression.

12 Claims, No Drawings

BENZODIOXANE DERIVATIVES

This application is a continuation of application Ser. No. 08/075,490, filed on as PCT/JP92/01366, Oct. 21, 1992, now abandoned.

TECHNICAL FIELD

This invention relates to novel benzodioxane derivatives represented by the general formula (I):

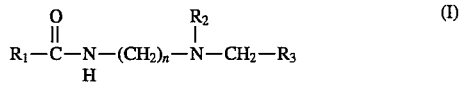

(where $R_1$ is an adamantyl group; $R_2$ is a hydrogen atom, a lower alkyl group, a lower alkenyl group or an aralkyl group; $R_3$ is a 1,4-benzodioxane ring that may optionally have 1–4 substituents selected from among a lower alkyl group, a lower alkoxy group, a halogen atom, an amino group, a hydroxyl group and a lower alkylcarbonyl group; n is an integer of 1–4). The novel benzodioxane derivatives of the present invention are useful as pharmaceuticals that exhibit pronounced antidepression and antianxiety effects.

BACKGROUND ART

Reflecting the ever increasing complexity of modern society, a growing number of patients suffer from psychosomatic diseases that can effectively be treated with antianxiety drugs. Further, a fairly high percentage of these patients also suffer from depression which manifests itself various in the form of physical symptoms. In many of those cases, antianxiety drugs alone are incapable of alleviating such symptoms. Thus, in order to ensure that a patient's symptoms are alleviated while allowing them to live an ordinary social life, the development of a drug is desired that is free from the side effects of existing antianxiety agents, such as sleepiness and dizziness and which yet have an antidepressant action.

Benzodiazepine based drugs have heretofore been used widely as antianxiety drugs. However, side effects such as sleepiness and dizziness occur unavoidably in drugs of this group. Several drugs have been reported to exhibit an antidepressant action but their efficacy is weak.

Serotonin based antianxiety drugs have recently been developed as alternatives to the benzodiazepine based drugs. It has been reported that the serotonin based drugs are generally superior to the benzodiazepine based drugs in that the side effects they cause, such as sleepiness and dizziness, are alleviated (Eison, Psychopathology, 989; 22 (Suppl. 1): 13–20). Among the reported serotonin based drugs, Buspirone is already sold on the market as an antianxiety drug that causes lesser side effects but, at the same time, it is known to have an antidepressant action (Robinson et al., Psychopathology, 1989; 22 (Suppl. 1): 27–36). Further, Ipsapirone (Glaser, Drugs of the Future, 13 (5) 429 (1988) and Gepirone (Jenkins et al., J. Clin. Pharmacol., 1990; 10 (3, Suppl.): 775–855) have also been reported as serotonin-based drugs that have both antianxiety and antidepressant effects.

Japanese Patent Public Disclosure No. Hei 2-15059 teaches that compounds represented by the general formula (II):

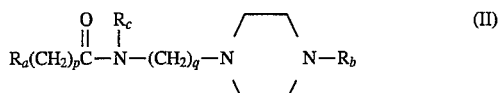

[where $R_a$ is 1-adamantyl, 3-methyl-1-adamantyl, 3-noradamantyl, unsubstituted or substituted 2-indolyl, 3-indolyl, 2-benzofuranyl or 3-benzofuranyl (a substituent, if any, is selected from among a lower alkyl, a lower alkoxy and a halogen): $R_b$ is an unsubstituted or substituted phenyl, benzyl, pyridinyl, pyrimidinyl or pyrazinyl (a substituent, if any, is selected from among a lower alkyl, a lower alkoxy, trifluoromethyl or a halogen); $R_c$ is hydrogen or a lower alkyl having 1–3 carbon atoms; p is an integer of 0 or 1; and q is an integer of 2–5] are useful as anxiety dispelling antidepressants.

All of these recently developed compounds are known to be antagonists for the serotonin 1A receptor. Drugs acting on this receptor are anticipated to work as antianxiety agents that are free from the side-effects of benzodiazepine based antianxiety agents and which yet lave an antidepressant action. Speaking of the serotonin receptor, it is known to play a role in counteracting the serotonin 2 receptor in the central nervous system (Gudelsky et al., Neuropharmacol., 1986, 25, 1307–1313; Davies et al., Soc. Neurosci. Abstr., 1987, 13, 801). Furthermore, two important facts have recently been reported: an antagonist against the serotonin 2 receptor exhibited an antianxiety action in an animal experiment (Stutzmann et al., Neurosclence Letters, 1991; 128, 4–8); and continuous administration of ipsaplrone caused a decrease in the intracerebral serotonin 2 receptor (Schechter et al., J. Pharmacol. Exptl. Ther. 1990; 225, 1335–1347). These facts suggest that in order to enhance the antianxiety and antidepressant actions of the antagonist for the serotonin 1A receptor, one may block the serotonin 2 receptor at the same time.

Disclosure of the Invention

The serotonin based antianxiety agents available today have various problems; for instance, Buspirone, Ipsapirone and Gepirone have only weak antidepressant and antianxiety effects and, further, these agents cause either lower ultromotivity (probably due to the dopamine antagonistic action) or serotonin syndrome (probably due to their nature as full agonists for the serotonin 1A receptor). Compared to Buspirone, the compounds represented by the general formula (II) exhibit stronger antidepressant and antianxiety effects but there still is room for improvement in their practical potency.

The present inventors conducted intensive studies in order to develop drugs that were free from the aforementioned problems of the prior art and which exhibited excellent antidepressant and antianxiety actions in combination and which yet caused less side effects. As a result, the inventors discovered compounds represented by the general formula (I) and this discovery has eventually led to the accomplishment of the present invention.

In the definition of the compounds of the present invention, the term "lower alkyl group" means an alkyl group having 1–6. preferably 1–4 carbon atoms, as exemplified by methyl, ethyl, n-propyl, i-propyl, n-butyl, i-butyl s-butyl and t-butyl. The term "lower alkoxy group" means an alkoxy group having 1–6 carbon atoms, as exemplified by methoxy, ethoxy, n-propoxy, i-propoxy, n-butoxy, i-butoxy, s-butoxy and t-butoxy. The term "halogen atom" means chlorine, bromine, fluorine and iodine, with chlorine being preferred.

The term "lower alkenyl group" means an alkenyl group having 2–6 carbon atoms, as exemplified by vinyl, allyl, 1-propenyl and 1-propenyl.

The term "aralkyl group" covers benzyl, benzhydryl, phenethyl, trityl, etc.

The term "lower alkylcarbonyl group" means an alkylcarbonyl group having 2–7 carbon atoms including the carbon atoms in the carbonyl moiety, as exemplified by acetyl, propionyl, butyryl, i-butyryl and pivaloyl.

The compounds represented by the general formula (I) can be produced in various ways, typically, according to the reaction schemes set forth below.

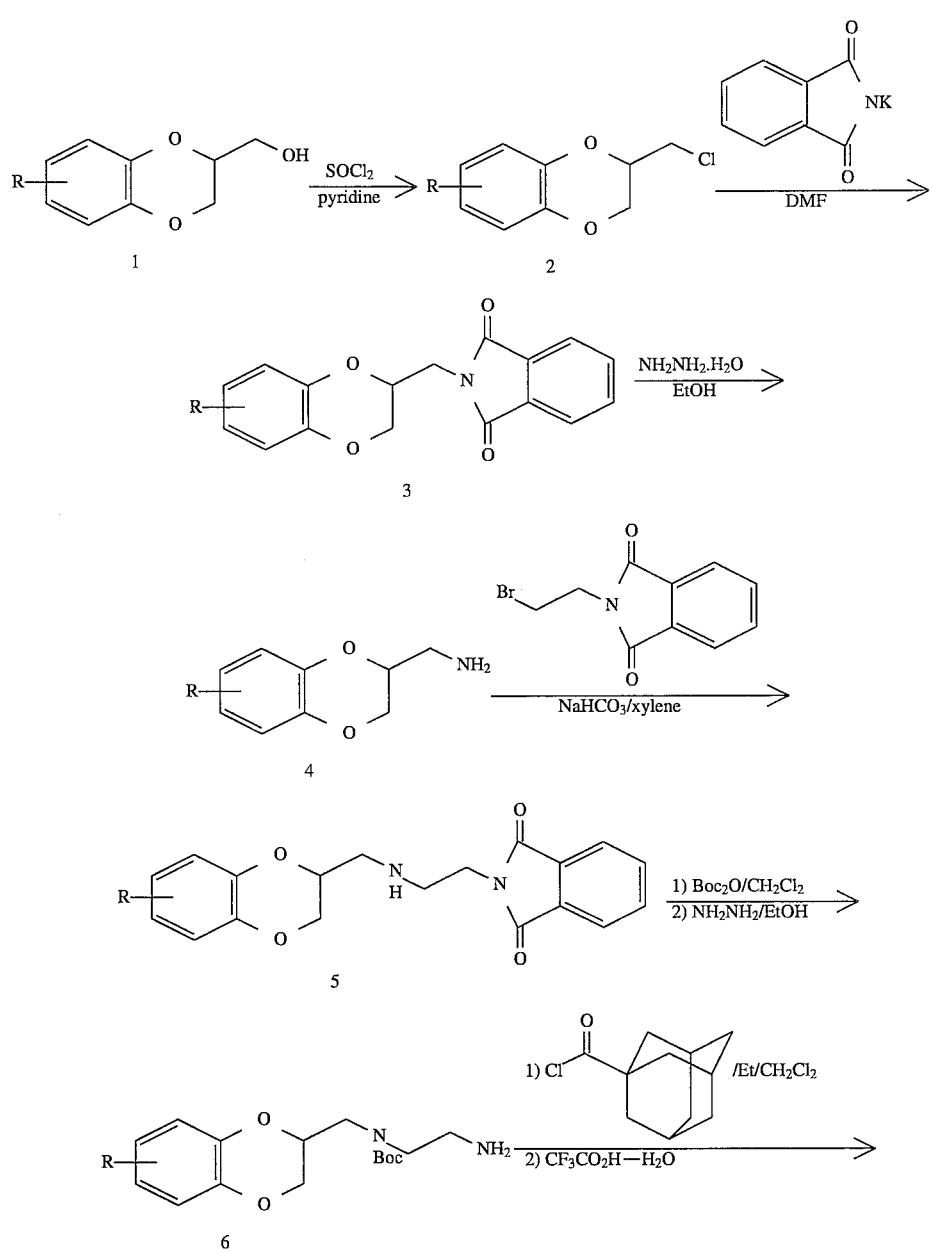

Reaction Scheme 1

-continued
Reaction Scheme 1

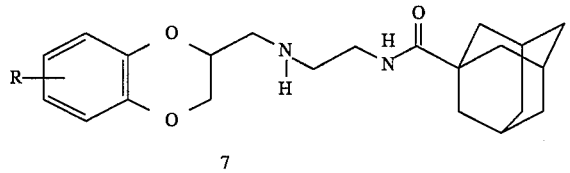

7

Reaction Scheme 2

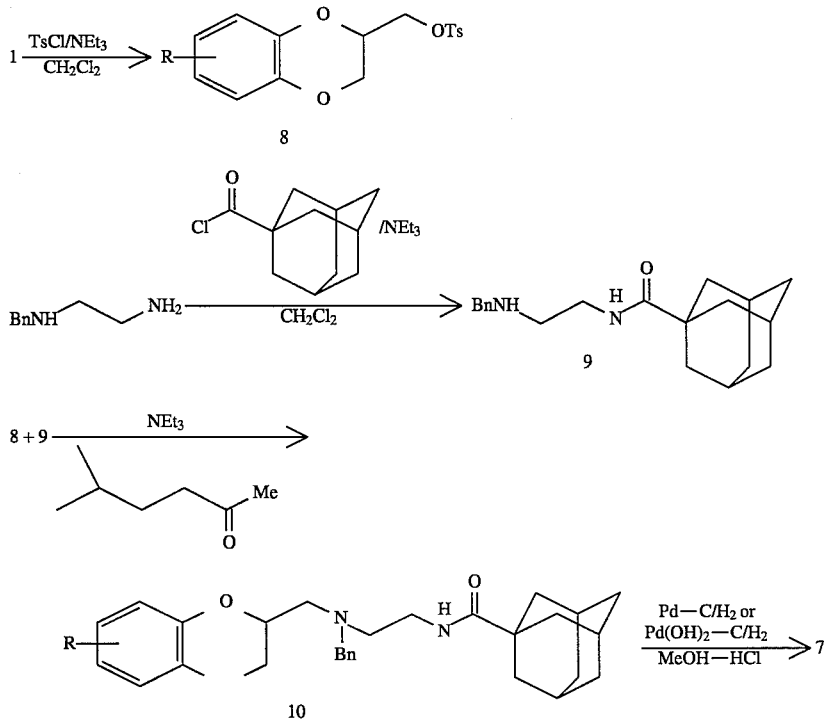

Reaction Scheme 3

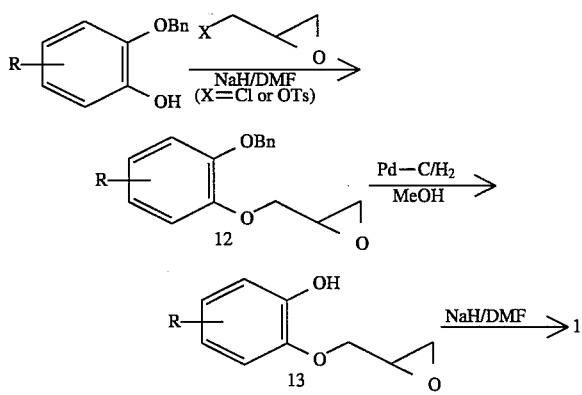

General method of synthesis 1 (Reaction scheme 1)

2-Hydroxymethylbenzodloxane derivative (compound 1) is reacted with thionyl chloride in pyridine at 100° C. for 1–4 h to give 2-chloromethyl-1,4-benzodioxane derivative (compound 2). The derivative is refluxed with phthalimide potassium salt under heating in N,N-dimethylformamide for 5–14 h to give compound 3. Thereafter, compound 3 is reacted with hydrazine hydrate either by standing at room temperature or by refluxing under heating for 1–14 h using an alcoholic solvent such as methanol, ethanol or isopropanol, preferably in methanol, thereby giving 2-aminomethylbenzoxane derivative (compound 4). The derivative is refluxed with N-bromoethyl phthalimide under heating in an inert solvent such as benzene, toluene or xylene, preferably in xylene, using a base such as sodium hydrogencarbonate, potassium carbonate or triethylamine, preferably in the presence of sodium hydrogencarbonate for 2–5 days, thereby giving compound 5. This compound is refluxed with di-t-butyl dicarbonate under heating in a solvent such as methylene chloride or chloroform, preferably in methylene chloride, for 2–4 h, whereby the secondary amine is t-butylcarbonylated. Subsequently, hydrazinc hydrate is added to the reaction system containing an alcoholic solvent such as methanol, ethanol or isopropanol, preferably ethanol, and the mixture is left to stand at room temperature or refluxed under heating for 1–14 h, thereby giving a primary amine form (compound 6). The amine form is reacted with 1-adamantanecarbonyl chloride in a solvent such as methylene chloride or chloroform, preferably in methylene chloride, in the presence of triethylamine, overnight at room temperature. Thereafter, the reaction mixture is stirred in trifluoroacetic acid for 0.5–1 h at room temperature, thereby yielding the end compound 7.

General method of synthesis 2 (Reaction scheme 2)

2-Hydroxymethyl-1,4-benzodioxane derivative (compound 1) is reacted with p-toluenesulfonyl chloride overnight at room temperature in an inert solvent such as methylene chloride or chloroform, preferably in methylene chloride, in the presence of a base such as triethylamine or N,N-diisopropylethylamine, preferably using triethylamine, thereby giving compound 8. In a separate step, N-benzylethylenediamine is reacted with 1-adamantanecarbonyl chloride at room temperature for 1–2 days in a solvent such as methylene chloride or chloroform, preferably in methylene chloride, in the presence of triethylamine, thereby giving compound 9. Compounds 8 and 9 are reacted at reflux temperature for 2–5 days using a base such as triethylamine, N,N-diisopropylethylamine, sodium hydrogencarbonate or potassium carbonate, preferably in the presence of triethylamine, in a solvent such as 5-methyl-2-hexanone, N,N-dimethylformamide, dimethyl sulfoxide, xylene or toluene, preferably in 5-methyl-2-hexanone, thereby giving compound 10. Compound 10 is reduced catalytically either at room temperature or under reflux in methanol, ethanol, or a methanol or ethanol solvent containing 10% conc. HCl, preferably in methanol containing 10% conc. HCl, in the presence of a Pd-C or Pd hydroxide-C catalyst, preferably in the presence of Pd hydroxide-C, thereby yielding the end compound 7.

The starting compound 1 may be prepared by a documented method (Augstein et al., J. Med. Chem., 1965 (8) 446) or by the following method of synthesis (Reaction scheme 3).

Monobenzyl catechol derivative (compound 11) is reacted with epichlorohydrin or glycidyl tosylate in an organic solvent such as N,N-dimethylformamide, methylene chloride or chloroform, preferably in N,N-dimethylformamide, in the presence of a base such as sodium hydride, sodium hydroxide or potassium hydroxide, preferably in the presence of sodium hydride, either at 100° C. for 1 h or at room temperature for 4–6 h, thereby giving compound 12. Compound 12 is hydrogenated catalytically in an organic solvent such as methanol, ethanol or ethyl acetate, preferably methanol, in the presence of Pd-C, at room temperature for 1–3 h, thereby removing benzyl. Further reaction is performed in an organic solvent such as N,N-dimethylformamide, methylene chloride or chloroform, preferably in N,N-dimethylformamide or chloroform, in the presence of a base such as sodium hydride, sodium hydroxide, potassium hydroxide or N,N-diisopropylethylamine, preferably in the presence of sodium hydride or N,N-diisopropylethylamine at a temperature in the range from room temperature to 100° C. for a period ranging from 1 to 12 h, thereby yielding the desired compound 1.

The compounds of the present invention which are represented by the general formula (I) are such that the carbon atom in the position of substitution on the 1,4-benzodioxane ring is asymmetric carbon; hence, the compounds may be available as optical isomers. If a substituent is present on the benzene ring of the 1,4-benzodioxane ring, the compounds are available as regio isomers. Such optical and regio isomers are also included within the scope of the present invention.

The compounds of the general formula (I) which are prepared in the manner described above may be in the form of pharmaceutically acceptable salts. Such salts can be prepared by reaction with suitable organic or inorganic acids and non-limiting examples are acid addition salts including hydrochloride, hydrobromide, sulfate, hydrogensulfate, phosphate, acetate, citrate, fumarate, gluconate, lactate, maleate and succinate.

The compounds of the general formula (I) which are prepared in the manner described above are such that, taken as a whole, they are comparable or superior to the existing antianxiety agents in each of the antidepressant and antianxiety effects; furthermore, those compounds cause less of the side effects which have occurred unavoidably in the administration of the existing antianxiety agents; therefore, the compounds of the present invention are expected to exhibit outstanding effects in the prevention and treatment of various diseases such as neurosis, psychosomatic diseases, autonomic imbalance and depression.

The compounds represented by the general formula (I) may be mixed with suitable additives such as excipients, auxiliaries, lubricants, antiseptics, stabilizers, humectants, emulsifiers, colorants, flavors and fragrances to formulate suitable preparations such as tablets, coated tablets, granules, subtilized granules, powders, capsules, syrups, elixirs, drops, solutions, suspensions and emulsions; these dosage forms may be administered either perorally or parenterally.

When the compounds of the general formula (I) are to be administered to humans, the dose of administration ranges typically from 1 to 30 mg, preferably from 5 to 10 mg, per day per adult.

EXAMPLES

The following examples are provided for the purpose of further illustrating the present invention but are in no way to be taken as limiting.

Example 1 (in accordance with the general method of synthesis 2)

Sodium hydride (90.2 mg; 2.25 mmol; 60% in oil) was washed with benzene, followed by addition of anhydrous N,N-dimethylformamide (5 ml). To the resulting suspension, 2-benzyloxy-3-methylphenol (457.3 mg, 2.137 mmol) dissolved in anhydrous N,N-dimethylformamide (5 ml) was added dropwise under a nitrogen atmosphere. To the resulting solution, glycidyl tosylate (506.2 mg, 2.220 mmol) dissolved in anhydrous N,N-dimethylformamide (5 ml) was added and the mixture was stirred for 4 h at room temperature. After the end of the reaction, ether (200 ml) was added to the solution and the reaction mixture was washed with a saturated aqueous solution of sodium chloride, followed by drying with anhydrous sodium sulfate and concentration under vacuum, thereby yielding a crude product as a pale brown oil (619.4 mg). The crude product was purified by column chromatography on silica gel using n-hexane/ethylacetate (6:1) as a mobile phase, thereby yielding 3-(2,3-epoxypropyl)-2-benzyloxytoluene (464.4 mg).

$^1$H-NMR (60 MHz,CDCl$_3$): δ7.5–7.0(m,5H), 6.8–6.5(m, 2H), 4.90(s,3H), 4.2–3.6(m,2H), 3.3–3.0 (m,1H), 2.8–2.5(m,2H), 2.10(s,3H)

The thus prepared epoxy compound (443.0 mg, 1.641 mmol) was dissolved in methanol (20 ml). To the resulting solution, 5% Pd-C (45.3 mg) was added and the mixture was subjected to catalytic hydrogenation at room temperature. After the end of the reaction, Pd-C was filtered off and the filtrate was concentrated under vacuum to give a crude product as a colorless crystal (323.9 mg). The crude product was purified by column chromatography on silica gel using n-hexane/ethyl acetate (6:1) as a mobile phase, thereby yielding 2-(2,3-epoxypropyl)-6-methylphenol as a colorless prism (233.8 mg).

$^1$H-NMR (60 MHz,CDCl$_3$): δ6.77(s,3H) , 6.10(brs,1H) , 4.5– 3.7(m,2H), 3.6–3.2(m,1H), 3.1– 2.7(m,2H), 2.30(s,3H)

The thus yielded product (198.0 rag, 1.100 mmol) was dissolved in anhydrous N,N-dimethylformamide (5 ml), followed by the addition of sodium hydride (65.0 mg, 1.625 mmol, 60% in oil). The resulting solution was stirred first at room temperature for 10 min, then at 100° C. for 1 h, followed by addition of water (20 ml) and extraction with ethyl acetate. The ethyl acetate layer was washed with a saturated aqueous solution of sodium chloride, followed by drying with anhydrous sodium sulfate and concentration under vacuum, thereby yielding a crude product as a brown oil. The crude product was purified by column chromatography on silica gel using n-hexane/ethyl acetate (6:1) as a mobile phase, thereby yielding 2-hydroxymethyl-8-methyl-1,4-benzodioxane as a colorless oil ( 97.2 rag).

$^1$H-NMR (60 MHz,CDCl$_3$): δ6.67(s,3H), 4.5–3.7(m,5H), 2.6– 2.2(br,1H), 2.20(s,3H)

The thus prepared benzodioxane derivative (97.2 mg, 0.540 mmol) was dissolved in methylene chloride (5 ml). To the resulting solution which was stirred at room temperature, p-toluenesulfonyl chloride (108.5 mg, 0.569 mmol) was added; then, triethylamine (1 ml ) was added, followed by continued stirring at room temperature for 2.5 h. After the end of the reaction, water (10 ml) was added to the solution and extraction was conducted with methylene chloride (200 ml). The methylene chloride layer was washed with water, followed by drying with anhydrous sodium sulfate and concentration under vacuum, thereby yielding a crude product as a brown oil. The etude product was purified by column chromatography on silica gel using n-hexane/ethyl acetate (2:1) as a mobile phase, thereby yielding 2-tosyloxymethyl-8-methyl-1,4-benzodioxane (124.6 mg).

In a separate step, 1-adamantanecarboxylic acid (1.1.45 g, 63.5 mmol) was dissolved in benzene (100 ml). To the resulting solution, thionyl chloride (9.07 g, 76.2 mmol) was added dropwise and, thereafter, the mixture was refluxed for 3 h. The solvent and excess thionyl chloride were distilled off under vacuum, thereby yielding a crude product of 1-adamanetancarbonyl chloride. Without further purification, the crude product was dissolved in methylene chloride (100 ml) and the resulting solution was added dropwise to a second solution at room temperature. The second solution had both N-benzylethylenediamine (9.54 g, 63.5 mmol) and triethylamine (7.07 g, 69.9 mmol) dissolved in methylene chloride (100 ml). The resulting liquid mixture was stirred at room temperature for 2 days before it was poured into water (300 ml); then, the mixture was stirred well and methylene chloride layer was separated. The remaining water layer was subjected to two runs of extraction with methylene chloride. The two methylene chloride layers were combined and washed with water twice, followed by drying with anhydrous sodium sulfate and concentration under vacuum. The resulting crude product was purified by column chromatography on silica gel using methylene chloride/methanol/ aqueous ammonia (200:25:1) as a mobile layer, thereby yielding N-{[2-(N-benzyl)amino] ethyl}tricyclo[3,3,1,1$^3$, $^7$]decane-1-carboxyamide (12.4 g).

$^1$H-NMR (60 MHz,CDCl$_3$): δ7.26(s,5H), 6.66(s,3H), 6.3–5.9(br,1H), 4.5–3.8(m,3H), 3.69(s,2H), 3.30(m,2H), 2.9–2.5(m,4H), 2.18(s,3H), 2.2–1.5(m,16H)

The amide compound (216.9 mg, 0.694 mmol), the already mentioned 2-tosyloxymethyl-8-methyl-1,4-benzodioxane (124.6 mg, 0.373 mmol) and triethylamine (70.9 mg, 0.702 mmol) were dissolved in 5-methyl-2-hexanone. The resulting solution was stirred under heating, first at 130° C. for 42 h, then at 150° C. for 9 h. Thereafter, water (20 ml) was added and the mixture was subjected to extraction with a methylene chloride/methanol (95:5) solvent system (150 ml). The organic layers were combined and washed with water, followed by drying with anhydrous sodium sulfate and concentration under vacuum to yield a crude product as a brown oil (474.9 mg). The crude product was purified by column chromatography on silica gel using n-hexane/ethyl acetate (6:1) as a mobile phase, thereby yielding N-{[2-(8-methyl 1,4-benzodioxan-2-ylmethyl)benzylamino] ethyl}tricyclo[3,3,1,$^3$, $^7$]decane-1-carboxyamide (compound a) in an amount of 56.1 mg.

$^1$H-NMR (60 MHz,CDCl$_3$): δ7.32 (s, 3H), 6.71(s,3H), 6.20– 5.90 (br, 1H), 4.40–3.80(m,3H), 3.72(s,2H), 3.50–3.10(m,2H), 3.00– 2.60(m,4H), 2.21(s,3H), 2.20–1.60(br ,16H)

The compound a (56.1 mg, 0.118 mmol) was dissolved in methanol. To the resulting solution, conc. HCl (0.2 ml) and 20% Pd hydroxlde-C (10 mg ) were added and catalytic hydrogenation was performed at room temperature. After the reaction, Pd was filtered off and the filtrate was concentrated under vacuum, yielding a crude product (201.6 mg) as a violet oil. The crude product was purified by column chromatography on silica gel using methylene chloride/ methanol/aqueous ammonia (200:25:1) as a mobile phase, thereby yielding N-{[2-(8-methyl-1,4-benzodioxan-2-ylmethyl)amino] ethyl}tricyclo[3,3,1,1$^3$, $^7$]decane-1-carboxyamide (38.7 mg) as a colorless oil.

$^1$H-NMR (60 MHz,CDCl$_3$): δ6.83(s,3H), 6.5–6.0(br,1H), 4.5– 3.8(m,3H), 3.45(m,2H), 3.05– 2.67(m,4H), 2.20(s,3H), 2.4– 1.4(br,16H)

The purified product (556.4 mg) was dissolved in a mixture of 4N HCl/dioxane solution (4 ml) and methanol (4 ml) and the resulting mixture was stirred for 5 min, followed by concentration under vacuum. The residue was recrystallized from chloroform/ethyl acetate (1:10), yielding a hydrochloride salt of the product (421.3 mg, compound 1) as a colorless prism. m.p. =129°–131° C.

Example 2 (in accordance with the general method of synthesis 1)

Commercial grade of 2-chloromethyl-1,4-benzodioxane (10.0 g, 54.7 mmol) and phthalimide potassium salt (12.0 g, 65.0 mmol) were added to N,N-dimethylformamide (350 ml) and subjected to reaction overnight under reflux; thereafter, N,N-dlmethylformamide was distilled off under vacuum. Water (250 ml) was added to the residue and the mixture was stirred well, with the floating solids being subsequently recovered by filtration. The solids were dried, then recrystallized from methanol/methylene chloride, thereby yielding (1,4-benzodioxan-2-ylmethyl)phthalimide as a colorless tabular crystal in an amount of 8.43 g. The thus obtained crystal was dissolved in ethanol (500 ml); to the solution, hydrazine hydrate (4.3 g) was added, followed by refluxing under heating for 3 h. The resulting solids were filtered off and ethanol was distilled off under vacuum, followed by addition of water (300 ml). Thereafter, an aqueous solution of 6N sodium hydroxide was added to adjust pH to 12 and the mixture was subjected to 3 cycles of extraction with methylene chloride. The methylene chloride layers were dried with anhydrous sodium sulfate, and concentrated under vacuum, thereby yielding a crude product of 2-aminomethyl-1,4-benzodioxane as a colorless oil (crude product, 4.3 g).

$^1$-NMR (60 MHz,CDCl$_3$): δ6.80(s,4H), 4.5–3.7(m,3H), 3.1– 3.8(m,2H), 1.70(brs,2H)

2-Aminomethyl-1,4-benzodioxane (3.33 g, 13.1 mmol) and N-(2-bromoethyl)phthalimide (4.3 g, 26.2 mmol) were dissolved in xylene (100 ml); to the resulting solution, sodium hydrogencarbonate (1.10 g, 13.1 mmol) was added and the mixture was refluxed under heating for 2 days. After the reaction, xylene was distilled off under vacuum and water (200 ml) was added, followed by three extractions with dichloromethane. The methylene chloride layer was dried with anhydrous sodium sulfate and concentrated under vacuum to yield a dark brown oil (8.7 g). This crude product was purified by column chromatography on silica gel using methylene chloride/methanol/aqueous ammonia (200:6:1) as a mobile phase, yielding N-[2-(1,4-benzodioxan-2-ylmethyl)amino] ethylphphalimide (1.24 g) as a brown oil.

The brown oil (500 mg, 1.5 mmol) was dissolved in methylene chloride (20 ml); to the resulting solution, a solution having sodium hydrogencarbonate (120 mg, 1.5 mmol) dissolved in water (10 ml) was added. To the resulting liquid mixture which was stirred vigorously at room temperature, a solution having di-t-butyl dicarbonate (320 mg, 1.5 mmol) dissolved in methylene chloride (2 ml) was added dropwise. The resulting solution was refluxed continuously under heating for 2 h; thereafter, the aqueous layer was separated, dried with anhydrous sodium sulfate and concentrated under vacuum, yielding a brown oil (920 mg). This product was dissolved in ethanol (10 ml) and hydrazine hydrate (0.22 ml) was added, followed by reflux under heating for 1 h. Ethanol was distilled off under vacuum and 6N aqueous sodium hydroxide (20 ml) was added, followed by three extractions with methylene chloride. The methylene chloride layers were combined and dried with anhydrous sodium sulfate; thereafter, the solvent was distilled off under vacuum to yield a crude product (480 rag). This product was purified by column chromatography on silica gel using methylene chloride/methanol/aqueous ammonia (200:25:1) as a mobile phase, thereby yielding a pale brown oil (320 mg, 1.04 mmol).

The oil was dissolved in methylene chloride (10 ml); to the resulting solution which was cooled with ice, a solution having 1-adamantanecarbonyl chloride (210 mg, 1.04 mmol) dissolved in methylene chloride (10 ml) was added dropwise, followed by addition of triethylamine (130 mg, 1.25 mmol). The resulting solution was stirred for 2 h at room temperature; thereafter, the solution was washed once with water, then with 2N HCl and 2N aqueous sodium hydroxide, dried with anhydrous sodium sulfate and concentrated under vacuum. The resulting colorless oil was dissolved in a liquid mixture of trifluoroacetic acid (5 ml) and water (0.5 ml) and the resulting reaction system was stirred at room temperature for 1 h. After the reaction, the solvent was distilled off under vacuum and the crude product was purified by column chromatography on silica gel using methylene chloride/methanol/aqueous ammonia (200:20:1) as a mobile phase, thereby yielding N-{[2-(1,4-benzodioxan -2-ylmethyl)amino]ethyl}tricyclo[3,3,1,1$^3$, $^7$]decane-1-carboxyamide (compound 2) as a colorless oil (300 mg).

$^1$H-NMR (60 MHz,CDCl$_3$): δ6.82(s,5H), 6.42(brt,1H,J= 4.0Hz), 4.45–3.90(m,3H), 3.5–3.15(m,2H), 3.0– 2.1(m,4H), 2.4–1.5(br,16H)

Example 3

2-Hydroxymethyl-6-methyl-1,4-benzodioxane (13.2 g, 73.3 mmol) was synthesized in accordance with the method described in Augstein et al., J. Med. Chem., 1965 (8) 446; it was then dissolved in anhydrous pyridine (6.38 g, 80.6 mmol). To the resulting solution which was cooled with a freezing mixture of salt and ice, thionyl chloride (11.34 g, 95.3 mmol) was added dropwise. After the end of dropwise addition, the mixture was stirred under heating at 105° C. for 5 h and poured into ice water (200 ml), followed by three extractions with ether. The ether layers were combined and washed with water twice, then dried with anhydrous magnesium sulfate and concentrated under vacuum, yielding a crude product as a brown oil (12.7 g). The crude product was purified by column chromatography on silica gel using methylenechloride-hexane (2:1) as a mobile phase, thereby yielding 3.8 g of 2-chloromethyl-6-methyl-1,4-benzodioxane as a yellow brown oil.

In the subsequent stage of synthesis, the method of Example 2 was repeated to yield 99 mg of N-{[2-(6-methyl-1,4-benzodioxan-2 ylmethyl)amino] ethyl}tricyclo[3,3,1,1$^3$, $^7$]decane-1-carboxyamide (compound 3) as a colorless oil.

$^1$H-NMR (60 MHz,CDCl$_3$): δ6.7(s,3H), 6.4–6.2(br,1H), 4.4– 3.9 (m, 3H), 3.36(m,2H), 3.0–2.7(m,4H), 2.3 ( s, 3H), 2.2–1.6(br, 16H)

Example 4

2-Hydroxymethyl-7-chloro-1,4-benzodioxane was synthesized in accordance with the method of Augstein et al., supra. Starting with this compound, the procedure described in Examples 2 and 3 were followed to yield N-{ [2-(7-chloro-1,4-benzodioxan-2ylmethyl)amino] ethyl}tricyclo[3,3,1,1$^3$, $^7$]decane-1-carboxyamide (compound 4) as a pale brown oil in an amount of 1.90 g.

$^1$H-NMR (60 MHz,CDCl$_3$): δ6.95–6.8(m,3H), 6.4–6.0(br,1H), 4.45–3.95(m,3H), 3.36(m,2H), 3.0– 2.6(m, 4H), 2.3–1.6(br,16H)

Example 5

A mixture of 2-hydroxymethyl-8-methoxy-1,4-benzodioxane and 2-hydroxymethyl-5-methoxy-1,4-benzodioxane was synthesized in accordance with the method of Augstein et al., supra. The mixture was converted to 2-aminomethyl form in accordance with the procedure described in Example 2. The mixture thus treated was isolated and purified by column chromatography on silica gel using methylene chloride/methanol (9:1) was a mobile phase, thereby yielding 1.08 g of 2-aminomethyl-8-methoxy-1,4-benzodioxane as a pale brown oil. In the subsequent stage of synthesis, the procedure described in Example 2 was followed to yield 7.5 mg of N-{[2-(8-methoxy-1,4-benzodioxan-2ylmethyl)amino] ethyl}tricyclo[3,3,1,1$^{3,7}$]decane-1-carboxyamide (compound 5).

$^1$H-NMR (60 MHz, CDCl$_3$): δ7.35–6.1(m,4H), 4.5-3.95(m,3H), 3.85(s,3H), 3.35(brt,2H), 3.1– 2.7(m,4H), 2.2–1.6(br,16H)

Example 6

2-Aminomethyl-5-methoxy-1,4-benzodioxane was isolated and purified by the method described in Example 5. Starting with this compound, the method described in Example 2 was repeated to yield 210 mg of N-{[2-(5-methoxy-1,4-benzodioxan-2-ylmethyl)amino]ethyl}tricyclo[3,3,1$^3$, $^7$]decane-1-carboxyamide (compound 6) as a colorless oil.

$^1$H-NMR (60 MHz, CDCl$_3$): δ6.9–6.2(m,4H), 4.45–3.95(m,3H), 3.32(m,2H), 3.0–2.5(m,4H), 2.1–1.4(br, 16H)

Example 7

The procedure of Example 1 was repeated except that (−)glycidyl tosylate was used in the process of synthesis, thereby yielding (−)-N-{[2- (8-methyl-1,4-benzodioxan-2ylmethyl)amino] ethyl}tricyclo[3,3,1$^3$, $^7$]decane-1carboxyamide hydrochloride (compound 7) (100% ee).

$^1$-NMR(200 MHz,CDCl$_3$): δ7.39 (brs,1H), 6.80–6.62(m, 3H), 4.92–4.79(br, 1H), 4.22 ( dd, 1H, J=11.4 and 2.9 Hz ), 4.01 (dd, 1H ,J=11.4 and 5.7 Hz), 3.8– 3.5 (br, 2H) , 3.4–3.1(br,5H), 2.28 (s,3H), 2.0(brs,3H), 1.83 (brs,6H), 1.68(brs,6H)
m.p.: 118°–119° C.
[α]$_D$=−28.33°

For optical purity measurement, an optically active column [Daicel OD; mobile phase=isopropanol/n-hexane (1:9)] was used and calculations were made on the basis of area ratio for the chart.

Example 8

The procedure of Example 1 was repeated except that (+)glycidyl tosylate was used in the process of synthesis, thereby yielding (+)-N-{[2-(8-methyl-1,4-benzodioxan-2ylmethyl)amino] ethyl}tricyclo[3,3,1,1$^3$, $^7$]decane-1-carboxyamide hydrochloride (compound 8) (90% ee). The NMR data of this compound were in agreement with those of the end compound prepared in Example 7.
m.p.: 119°–120° C.
[α]$_D$=+25.41°

Example 9

The end product (compound 1) of Example 1 (1.34 g, 3.5 mmol) was dissolved in N,N-dimethylformamide (20 ml). To the resulting solution, potassium carbonate (0.58 g, 4.2 mmol) and allyl bromide (0.51 g, 4.2 mmol) were added and the resulting mixture was stirred for 16 h at 50° C. Ice water (100 ml) was added to the reaction solution, which was then extracted with ethyl acetate three times and washed with water twice, followed by drying with anhydrous magnesium sulfate. The solvent was distilled off under vacuum, thereby yielding 1.28 g of a crude product as a pale brown oil.

A portion (0.2 g) of the crude product was purified by column chromatography on silica gel using methylene chloride/methanol/aqueous ammonia (200:2:1) as a mobile layer, thereby yielding N-{[2-(8-methyl-1,4-benzodioxan -2-ylmethyl)allylamino]ethyl}tricyclo[3,3,1$^3$, $^7$]decane-1 -carboxyamide (compound 9) as a colorless oil (0.14 g).

$^1$-NMR (60 MHz,CDCl$_3$): δ66.71(s,3H), 6.40–6.10(br, 1H), 6.00–5.50(m,1H), 5.40– 5.20 (m, 2H), 5.20–5.00 (m, 1H), 4.50– 3.90(m,3H), 3.50–3.10(m,4H), 3.00–2.60(m, 4H), 2.20(s,3H), 2.20– 1.60(br,16H)

Example 10

The crude product of Example 9 (1.08 g, 2.5 mmol) was dissolved in methanol (30 ml). To the resulting solution, 5% Pd-C (100 mg) was added and the mixture was subjected to catalytic hydrogenation with 1 atm. hydrogen gas at room temperature. After the reaction, Pd was filtered off and the filtrate was concentrated under vacuum, yielding a crude product as a colorless oil (0.9 g).

The crude product was purified by column chromatography on silica gel using methylene chloride/methanol/aqueous ammonia (200:2:1) as a mobile phase, thereby yielding N-{[2-(-8-methyl-1,4-benzodioxan-2-ylmethyl propylamino]ethyl}tricyclo[3,3,1,1$^3$, $^7$]decane-1-carboxyamide (compound 10) as a colorless oil (0.58 g).

$^1$H-NMR (60 MHz,CDCl$_3$): δ6.72(s,3H), 6.40–6.00(br, 1H), 4.50–3.90(m,3H), 3.50– 3.20(m,2H), 3.00–2.40(m, 6H), 2.20(s,3H), 2.20–1.50(br,18H), 0.93 ( t, J=6.0 Hz, 3H )

Example 11

2-Hydroxymethyl-5,8-dimethyl-1,4-benzodioxane was synthesized in accordance with the method of Augstein et al. Starting with this compound, the procedure of Example 2 and 3 were repeated to yield N-{[2-(5,8-dimethyl-1,4-benzodioxan-2-ylmethyl) amino]ethyl}tricyclo[3,3,1$^3$, $^7$]decane-1-carboxyamide (compound 11) as a pale brown oil (0.387 g).

$^1$-NMR(270 MHz,CDCl$_3$): δ6.61(s,2H), 6.18(brs,1H), 4.34– 4.22(m,2H), 4.09–3.96(m,1H), 3.42–3.29 (m, 2H), 2.99–2.76 (m, 4H), 2.16(s,6H), 2.09–1.63(m,16H)

Example 12

The procedure of Example 11 was repeated except that 2-hydroxymethyl-7-nitro-1,4-benzodioxane was used as the starting compound. As a result, N-{[2-(7-amino-1,4-benzodioxan-2-ylmethyl) amino]ethyl}tricyclo[3,3,1,1$^3$, $^7$]decane-1-carboxyamide (compound 12) was produced as a pale brown oil ( 0.55 g).

$^1$H-NMR (60 MHz, CDCl$_3$): δ6.80–6.50(m,1H) , 6.40–6.00(m,3H), 4.40–3.80 (m, 3H) , 3.45–3.10(m,2H), 3.00–2.40 (m, 4H) , 2.20–1.50(br ,18H)

Example 13

The procedure of Example 11 was repeated except that 2-hydroxymethyl-7-isobutyl-1,4-benzodioxane was used as the starting compound. As a result, N-{[2-(7-isobutyl-1,4 -benzodioxan-2ylmethyl) amino]ethyl}tricyclo[3,3,1,1$^3$, $^7$]decane-1 -carboxyamide (compound 13) was produced as a pale brown oil (0.48 g).

$^1$H-NMR(200 MHz,CDCl$_3$): δ6.80–6.56(m,3H), 6.20–6.10(brs,1H), 4.32–3.92(m,3H), 3.40–3.20(m,2H), 2.92–2.76(m,4H), 2.35(d,J=6.9Hz,1H), 2.08–1.52(m,18H), 0.92 (d, J=6.9Hz, 6H)

Example 14

The procedure of Example 11 was repeated except that 2-hydroxymethyl-7-methoxy-1,4-benzodioxane was used as the starting compound. As a result, N-{[2-(7-methoxy-1,4-benzodioxan-2-ylmethyl) amino]ethyl}tricyclo[3,3,1,1$^3$, $^7$]decane-1-carboxyamide (compound 14) was produced as a pale brown oil (0.71 g).

¹H-NMR (60 MHz,CDCl₃): 7.00–6.30(m,3H), 6.40–6.00(br,1H), 4.40–3.90(m,3H), 3.75(s,3H), 3.60–3.20(m,2H), 3.00–2.70(m,4H),2.20–1.60(br,16H)

Example 15

The procedure of Example 11 was repeated except that 2-hydroxymethyl-8-acetyl-1,4-benzodioxane was used as the starting compound. As a result, N-{[2-(8-acetyl-1,4benzodioxan-2ylmethyl)amino] ethyl}tricyclo[3,3,1,1³, ⁷]decane-1-carboxyamide (compound 15) was produced as a pale brown oil (0.437 g).

¹H-NMR (60 MHz,CDCl₃): δ7.51–7.16(m,2H), 6.90–6.66(m,1H), 6.12(brs,1H), 4.39–3.86(m,3H), 3.47–3.06(m,2H), 2.94–2.55(m,4H), 2.41(s,3H), 2.12–1.28(m, 16H)

Example 16

The procedure of Example 11 was repeated except that 2-hydroxymethyl-6-benzyloxy-1,4-benzodioxane was used as the starting compound. As a result, N-{[2-(6-hydroxy-1,4-benzodioxan-2 ylmethyl)amino] ethyl}tricyclo[3,3,1,1³, ⁷]decane-1-carboxyamide (compound 16) was produced as a pale brown oil (0.74 g).

¹H-NMR(200 MHz,CDCl₃): δ6.72–6.20(m,3H), 4.28–3.88(m,3H), 3.88–3.50(brs,2H), 3.42–3.28(m,2H), 2.92–2.72(m,4H), 2.08–1.46(m,16H)

Example 17

The procedure of Example 11 was repeated except that 2-hydroxymethyl-7-benzyloxy-1,4-benzodioxane was used as the starting compound. As a result, N-{[2 -(7-hydroxy-1,4-benzodioxan-2ylmethyl)amino] ethyl}tricyclo[3,3,³, ⁷]decane-1-carboxyamide (compound 17) was produced as a pale brown oil (1.57 g).

¹H-NMR(270 MHz,CDCl₃): δ6.70–6.33(m,4H), 4.30(brs,1H), 4.15(d,j=9.9Hz,2H), 3.93–3.86(m,1H), 3.60–3.26(m,2H), 3.18–2.78(m,4H), 2.01–1.69(m,16H)

Example 18

The procedure of Example 11 was repeated except that 2-hydroxymethyl-8-benzyloxy-1,4-benzodioxane was used as the starting compound. As a result, N-{[2-(8 -hydroxy-1,4-benzodioxan-2ylmethyl)amino] ethyl}tricyclo[³,³,¹,¹³, ⁷]decane -1-carboxyamide (compound 18) was produced as a pale brown oil (0.69 g).

¹H-NMR(270 MHz, CDCl₃): δ6.74–6.41(m,3H) 6.18 (brs, 1H), 4.32–4.22 (m, 2H) 4.03–3.96 (m, 1H), 3.40–3.36 (m, 2H) 2.98–2.75 (m, 4H), 2.20–1.65 (m, 17H)

Example 19

The procedure of Example 11 was repeated except that 2-hydroxymethyl-5-benzyloxy-1,4-benzodioxane was used as the starting compound. As a result, N-{[2-(5-hydroxy-1,4-benzodioxan-2ylmethyl)amino] ethyl)tricyclo[3,3,1,1³, ⁷]decane-1-1-carboxyamide (compound 19) was produced as a pale brown oil (0.45 g).

¹H-NMR (270 MHz, CDCl₃): δ6.75–6.42 (m, 3t{) , 6.16(brs,1H), 4.33–4.24 (m, 2H), 4.09–4.02(m,1H), 3.39–3.32 (m, 2H), 2.97–2.79(m,4H), 2.03–1.66 (m, 17H)

Example 20

The procedure of Example 11 was repeated except that 2-hydroxymethyl-6,8-dimethyl-1,4-benzodioxane was used as the starting compound. As a result, N-{[2(6,8-dimethyl-1,4-benzodioxan-2 ylmethyl)amino] ethyl)tricyclo[3,3,1,1³, ⁷]decane-1 -carboxyamide (compound 20) was produced as a pale brown oil (0.93 g).

¹H-NMR(200 MHz,CDCl₃): δ6.52(s,2H), 6.24–6.08(brs, 1H), 4.28–3.92(m,3H), 3.40–3.28(m,2H), 2.92–2.76(m,4H), 2.20(s,3H), 2.16(s,3H), 2.08–1.52(m,16H)

Test Example 1

Affinity for intracerebral serotonin 1A and serotonin 2 receptor was checked in accordance with the method of Hall et al. (J. Neurochem., 44, 1685–1695, 1985) and the method of Leysen et al. (Mol. Pharmacol., 21, 301–314, 1982).

Stated more specifically, the cortex and hippocampal tissue were extracted from the brain of 7-wk old S.D. line male rats, mixed with 20 volumes of Tris-HCl buffer (50 mM, pH 7.7) and homogenized with a Teflon homogenizer. Thereafter, the homogenate was centrifuged at 39800×g for 20 min and the supernatant was discarded. Forty volumes of a buffer were added to the precipitate and the mixture was homogenized with a Polytron homogenizer, with the homogenate being centrifuged under the same condition as set forth above. The same procedure was repeated two more times and the final precipitate was homogenized with 40 volumes of a buffer; thereafter, the homogenate was stored at least overnight at −80° C. On the day when binding experiments were to be conducted, the homogenate was thawed at room temperature and incubated at 37° C. for 20 min to remove the endogenous serotonin.

Thereafter, centrifugation was conducted at 39800×g for 20 min and 40 volumes of a buffer were added to the precipitate, followed by homogenization. This procedure was repeated three times; to the final precipitate, a buffer was added in 65 volumes for the case of serotonin 1A receptor and in 80 volumes for the case of serotonin 2 receptor and the mixture was homogenized in preparation for the binding experiments that are described below. All procedures of experimentation except storage in a frozen state and thawing at room temperature were conducted at 4° C. or below.

The compounds tested in all the test examples described below are keyed as shown in the following table.

| Control compounds | |
| --- | --- |
| Buspirone | Commercial antianxiety agent |
| WY-50324 | Example 2 of Japanese Patent Public Disclosure No. Hei 2-15059 |
| SM-3997 | Example 2 of Japanese Patent Public Disclose No. Sho 58-126865 |
| MDL-73005 | Example 9 of Japanese Patent Public Disclosure No. Sho 61-246180 |
| Compounds of the Invention | |
| Compound 2 | Example 2 |
| Compound 5 | Example 5 |
| Compound 1 | Example 1 |
| Compound 6 | Example 6 |
| Compound 3 | Example 3 |
| Compound 4 | Example 4 |
| Compound 7 | Example 7 |
| Compound 8 | Example 8 |
| Compound 9 | Example 9 |
| Compound 10 | Example 10 |

-continued

| Compound | Example |
|---|---|
| Compound 11 | Example 11 |
| Compound 12 | Example 12 |
| Compound 13 | Example 13 |
| Compound 14 | Example 14 |
| Compound 15 | Example 15 |
| Compound 16 | Example 16 |
| Compound 17 | Example 17 |
| Compound 18 | Example 18 |
| Compound 19 | Example 19 |
| Compound 20 | Example 20 |
| Compound a | Example 1 (intermediate) |

Serotonin 1A receptor binding experiment

A reaction solution containing 0.5 nM (final concentration) of 3H-8-hydroxy-2-(di-n-propylamino)tetralin (8-OH-DPAT), 0.14 ascorbic acid and 500 μl of brain homogenate in 1.0 ml (final volume) of a buffer was incubated at 25° C. for 30 min. Thereafter, the reaction solution was filtered by rapid passage through a glass filler. The filter was washed rapidly with an ice-cooled buffer (3 ml) three times, put into a scintillation vial together with a scintillation cocktail, and left to stand overnight at 4° C. On the next day, the vial was agitated well and measurements were conducted with a scintillation counter. To determine the amount of specific binding, the amount of binding in the presence of excess unlabeled serotonin (10 μM) was subtracted from the total amount of binding. As an index for the affinity of a test compound for either receptor, the concentration at which the specific binding of $^3$H-DPAT was inhibited by 50% ($IC_{50}$, M) was determined using computer software EBDA/LIGAND (Biosoft).

Serotonin 2 receptor binding experiment

A reaction solution containing 0.5 nM (final concentration) of $^3$H-ketancerine and 500 μl of brain homogenate in 1.0 ml (final volume) of a buffer was incubated at 30° C. for 30 min. Subsequent procedures were the same as in the serotonin 1A receptor binding experiment and $IC_{50}$ (M) was determined accordingly. To determine the amount of specific binding, the amount of binding in the presence of excess unlabelled methysergide (2 nM) was subtracted from the total amount of binding. As is clear from Table 1 below, the test compounds of the present invention showed higher affinity for the serotonin A and serotonin 2 receptors than did the existing drugs, thus suggesting the potent antianxiety and antidepressant activities of those compounds.

TABLE 1

| Compound | $-logIC_{50}$ 5-HT$_{1A}$ | $-logIC_{50}$ 5-HT$_2$ |
|---|---|---|
| Buspirone | 7.70 | <6.00 |
| WY-50324 | 8.90 | 6.70 |
| SM-3997 | 7.50 | 6.26 |
| MDL-73005 | 7.44 | <6.00 |
| Comp. | | |
| 2 | 6.52 | 7.45 |
| 5 | 9.46 | 8.00 |
| 1 | 8.93 | 7.52 |
| 6 | 8.39 | 7.12 |
| 3 | 8.60 | 7.63 |
| 4 | 8.29 | 7.37 |
| 7 | 9.50 | 7.80 |
| 8 | 8.20 | 7.30 |

TABLE 1-continued

| Compound | $-logIC_{50}$ 5-HT$_{1A}$ | $-logIC_{50}$ 5-HT$_2$ |
|---|---|---|
| 9 | 8.4 | 6.0 |
| 10 | 8.0 | 6.2 |
| 11 | 8.4 | 7.1 |
| 12 | 9.4 | 6.7 |
| 13 | 7.2 | 6.5 |
| 14 | 9.4 | 7.6 |
| 15 | 8.5 | 7.2 |
| 16 | 8.6 | 6.8 |
| 17 | 9.6 | 6.6 |
| 18 | 9.8 | 7.3 |
| 19 | 8.2 | 6.0 |
| 20 | <7.5 | 6.7 |
| a | 6.8 | <6.0 |

Test Example 2

Antidepressant effect

An antidepression test was conducted in accordance with the method of Porsolt et al. (Europ. J. Pharmacol., 47, 379–391, 1978). Stated more specifically, 7-wk old S.D. line male rats were placed in a glass cylinder (18 cm$^\Phi$×40 cm$^H$) for 15 min. The cylinder was filled with water (25° C.) to a depth of 15 cm. Thereafter, the rats were placed in a hot environment (32° C.) for 15 min before they were returned to the cage. Twenty-four hours later, the rats were compelled again to swim in the same cylinder for 5 min and the total time over which the rats remained motionless was measured. A test drug was administered perorally to each animal 30 min before it was compelled to swim for 5 min. Antidepressant agents are known to be capable of specifically reducing the time over which the rats would remain motionless (Psyehopharmaeol., 83, 1–16, 1984, and ibid., 94, 147–160, 1988). The antidepressant effect was calculated by the following formula:

$$100 - \frac{\text{(the time over which the treated group remained motionless)}}{\text{(the time over which the control group remained motionless)}} \times 100.$$

Table 2 below shows the efficacy of each test compound as it was administered in an amount of 20 mg/kg. Obviously, compounds 2, 5, 1, 6 and 18 exhibited better antidepressant effects than WY-50324. In addition, test compounds 3, 4 and 12 showed almost comparable effects to WY-50324. In contract, MI)L-73005 had an extremely weak antidepressant effect. When the value of $ED_{50}$ (the dose at which the time over which rats remained motionless could be reduced by one half the time in the ease of the control groups) was determined by the probit method, compound 1 was found to have three times the activity of WY-50324; the $ED_{50}$ of compound 1 was 8.1 mg/kg whereas that of WY-50324 was 24.3 mg/kg.

TABLE 2

Antidepressant effect upon peroral administration of 20 mg/kg

| Drug | Efficacy | Drug Comp. | Efficacy |
|---|---|---|---|
| WY-50324 | 58.1 ± 5.0 | 2 | 85.0 ± 8.5 |
| Buspirone | −25.2 ± 3.9 | 5 | 97.6 ± 0.9 |
| SM-3997 | −10.5 ± 10.6 | 1 | 72.0 ± 5.5 |
| MDL-73005 | 28.3 ± 10.9 | 6 | 82.2 ± 6.6 |
| | | 3 | 56.8 ± 9.0 |
| | | 4 | 51.9 ± 8.2 |
| | | 12 | 57.0 ± 5.9 |
| | | 14 | 46.9 ± 7.1 |
| | | 18 | 78.5 ± 4.5 |

TABLE 3

Antianxiety effect upon peroral administration of 20 mg/kg

| Drug | Efficacy | Drug Comp. | Efficacy |
|---|---|---|---|
| WY-50324 | 46.9 ± 6.3 | 2 | 39.3 ± 10.8 |
| Buspirone | 37.5 ± 4.7 | 5 | 40.9 ± 7.3 |
| SM-3997 | 48.5 ± 15.8 | 1 | 85.4 ± 10.3 |
| MDL-73005 | 67.6 ± 5.5 | 6 | 28.7 ± 9.5 |
| | | 3 | 63.9 ± 6.8 |
| | | 4 | 76.8 ± 13.7 |
| | | 16 | 46.5 ± 4.7 |
| | | 17 | 66.6 ± 8.7 |
| | | 18 | 80.1 ± 6.1 |

Test Example 3

Antianxiety effect

Antianxiety test was conducted in accordance with a method adapted from the method of Vogel et al. (Psychopharmacol., 21, 1–7, 1971). Stated more specifically, S.D. line male rats weighing 250–300 g were entirely kept from water for 24 h and then placed in a concrete experimental box. The experimental box (25× 17×15 cm) had a water supply nozzle in the center of the front wall 2 cm above the bottom; the nozzle was connected to a water bottle in such a way that the quantity of water drunk (the number of water drops) could be measured. The bottom of the box was made of a stainless steel grid, from which electric shock (0.2 mA, 0.5 sec) could be applied to the limbs of rats. The test schedule was as follows: first, the rats were acclimatized to the experimental box and trained for drinking water; this was done for 3 min without electric shock. The quantity of water drunk by the rats was then measured (under non-punishment). Then, the rats were kept from drinking water for 24 h. Thereafter, the quantity of water drunk by each rat was measured (before administration of test compound) under such conditions that an electric shock was applied each time a rat drank one water drop (under punishment). Thirty minutes later, a test drug was administered perorally and after an additional 20 min, the quantity of water drunk by each rat was again measured under punishment (after administration of test compound). The quantity of water drunk by rats will decrease under punishment but it is known that the initial level can be restored by administering an antianxiety agent.

The antianxiety effect of a test compound was calculated by the following formula:

$$\frac{\left(\begin{array}{c}\text{the quantity of water}\\\text{drunk after adminis-}\\\text{tration of test drug}\end{array}\right) - \left(\begin{array}{c}\text{the quantity of water}\\\text{drunk before adminis-}\\\text{tration of test drug}\end{array}\right)}{\left(\begin{array}{c}\text{the quantity of water}\\\text{drunk under non-}\\\text{punishment}\end{array}\right) - \left(\begin{array}{c}\text{the quantity of water}\\\text{drunk before adminis-}\\\text{tration of test drug}\end{array}\right)} \times 100$$

Table 3 shows the antianxiety effect of each test compound as it was administered in a dose of 20 mg/kg. Obviously, compounds 1 and 18 exhibited better effects than MDL-73005 whereas compounds 3, 4 and 17 exhibited comparable effects to MDL-73005. In addition, compounds 2, 5 and 16 exhibited almost comparable effects to WY-50324.

Test Example 4

Sedative action

Seven-week old male S.D. line rats were administered a test drug perorally and after the passage of 30 min, the amount of spontaneous movement of the rats was measured for 10 min by means of Animex.

The results are shown in Table 4. Buspirone as administered in amounts of 20 mg/kg and more could lower the amount of spontaneous movement in a dose-dependent fashion. However, compound 1, WY-50324 and MDL-73005 had no effects ultromotivity; in other words, those compounds had no appreciable sedative action.

TABLE 4

Amount of Spontaneous Movement (Counts/10 min) Dose

| Drug | control | 20 mg/kg | 40 mg/kg | 60 mg/kg |
|---|---|---|---|---|
| Buspirone | 405.2± 47.7 | 253.3 ± 30.0* | 163.4 ± 38.0** | 115.0 ± 26.0** |
| WY-50324 | 405.2± 47.7 | 315.5 ± 20.0 | 361.9 ± 16.9 | 401.6 ± 31.4 |
| Comp. 1 | 405.2± 47.7 | 442.0 ± 31.1 | 401.8 ± 52.8 | 319.4 ± 27.8 |
| MDL-73005 | 405.2± 47.7 | 395.8 ± 41.5 | 331.5 ± 40.1 | 335.0 ± 22.8 |

*$p < 0.05$,
**$p < 0.01$ vs control

Test Example 5

Antidopamine action

Seven-week old male S.D. line rats were administered a test drug perorally and after the passage of 30 min, the dopamine agonist apomorphine was injected subcutaneously in an amount of 0.5 mg/kg. For the subsequent 5–30 min period, the intensity of stereotypic behavior that was induced in the rats by apomorphine was measured six times at 5-min intervals by a scoring method and the sum of the scores was determined (for a maximum of 24).

The results are shown in Table 5. Obviously, the stereotypic behavior induced by apomorphine was intensely compelled by Buspirone. In addition, WY-50324 showed an inhibitory action in high doses. However, compound 1 had no effect at all when it was used in a dose of 20 mg/kg. Therefore, one may safely conclude that compound 1 has no antidopamine action.

TABLE 5

| Drug | Apomorphine Induced Stereotypic Behavior | | | |
|---|---|---|---|---|
| | control | 10 mg/kg | 20 mg/kg | 40 mg/kg |
| Buspirone | 14.4± 0.9 | 10.3 ± 0.6* | 0.7 ± 0.2** | 0.2 ± 0.2** |
| WY-50324 | 14.4± 0.9 | 14.7 ± 1.2 | 12.1 ± 0.7 | 10.9 ± 0.4** |
| Comp. 1 | 16.0± 1.1 | — | 14.7 ± 1.2 | — |

*$p < 0.05$,
**$p < 0.01$ vs control

Test Example 6

The procedure of Test Examples 2 and 3 were repeated except that test compounds were administered perorally in a dose of 10 mg/kg. The antianxiety and antidepressant effects of the test compounds are shown in Table 6 below.

TABLE 6

| | Antianxiety and Antidepressant Effects Upon Peroral Administration of 10 mg/kg | |
|---|---|---|
| Drug Comp. | Antianxiety | Antidepressant |
| 1 | 42.4 ± 2.1 | 66.7 ± 12.6 |
| 7 | 45.4 ± 3.4 | 62.7 ± 12.4 |
| 12 | 52.1 ± 2.5 | — |

The above data demonstrate the superiority of compounds 1, 7 and 12 of the present invention. Among them, compound 7 is particularly preferred.

Test Example 7

The procedures of Test Example 2 and 3 were repeated, except that test compounds were administered perorally in a dose of 20 mg/kg to check the longevity of their antianxiety and antidepressant effects for 0.5, 2 and 4 h. The results are shown in Table 7 below.

TABLE 7

| | | Longevity of the Antianxiety and Antidepressant Effects Upon Peroral Administration of 20 mg/kg | | | |
|---|---|---|---|---|---|
| | Time after administration, h | Test Drug | | | |
| | | WY-50324 | MDL-73005 | Comp. 1 | Comp. 7 |
| Antianxiety effect | 0.5 | 57.8 ± 10.0 | 44.9 ± 4.5 | 52.8± 6.7 | 66.0± 10.9 |
| | 2.0 | 24.8 ± 2.2* | 17.0 ± 1.9* | 48.2± 4.9 | 51.6± 4.8 |
| | 4.0 | 11.2 ± 2.0* | 8.1 ± 0.8* | 29.5± 2.2 | 26.1± 2.0 |
| Antidepressant effect | 0.5 | 56.7 ± 7.2 * | — | 71.8± 4.8 | 72.1± 6.2 |
| | 2.0 | 17.3 ± 7.3* | — | 73.9± 5.6 | 76.9± 5.1 |
| | 4.0 | 0.7 ± 3.2* | — | 40.7± 8.8 | 38.1± 8.7 |

*$p < 0.01$ (vs compound 7)

Industrial Applicability

The compounds of the present invention which are represented by the general formula (I) have both antianxiety and antidepressant actions and yet they cause less side effects. Therefore, the compounds can be used as excellent drugs that are highly effective in the prevention and treatment of various diseases such as neurosis, psychosomatic diseases, autonomic imbalance and depression.

We claim:

1. A compound of N-[[2-(8-methyl-1,4-benzodioxan-2-ylmethyl) amino]ethyl]tricyclo[3,3,1,1$^3$, $^7$] decane-1-carboxyamide or a salt thereof.

2. The compound of claim 1, which is (–)-N-[[2-(8-methyl-1,4-benzodioxan-2-ylmethyl) amino]ethyl]tricyclo [3,3,1,1$^3$,$^7$] decane-1-carboxyamide.

3. The compound of claim 1, wherein said salt is a pharmaceutically acceptable salt.

4. The compound of claim 1, wherein said salt is a pharmaceutically acceptable hydrochloride.

5. A pharmaceutical composition comprising:

an effective amount of a compound of N-[[2-(8-methyl-1,4-benzodixan-2-ylmethyl)amino] ethyl]tricyclo[3,3, 1,1$^3$,$^7$]decane-1-carboxyamide or a pharmaceutically acceptable salt thereof; and a pharmaceutically acceptable carrier thereof.

6. The pharmaceutical composition of claim 5, wherein said compound is (–)-N-[[2-(8-methyl-1,4-benzodioxan-2ylmethyl)amino] ethyl]tricyclo[3,3,1,1$^3$,$^7$] decane-1-carboxyamide.

7. A method of treating depression in a patient in need of such treatment, the method comprising:

administering to said patient an effective anti-depressant amount of a compound of N-[[2-8-methyl-1,4-benzodioxan-2-ylmethyl)amino ]ethyl]tricyclo[3,3,1,1$^3$, $^7$]decane-1-carboxyamide, or a pharmaceutically acceptable salt thereof.

8. The method of claim 7, wherein said pharmaceutically acceptable is a hydrochloride.

9. The method of claim 7, wherein said compound is (–)-N-[[2-(8-methyl-1,4-benzodioxan-2-ylmethyl amino] ethyl]tricyclo[ -3,3,1,1$^3$,$^7$] decane-1-carboxyamide.

10. The method of treating anxiety in a patient in need of such treatment, the method comprising:

administering to said patient an effective anti-anxiety amount of a compound of N-[[2-(8-methyl-1,4-benzodioxan-2-yl-methyl)amino]ethyl] tricyclo[3,3,1,1$^3$,$^7$] decane-1-carboxyamide, or a pharmaceutically acceptable salt thereof.

11. The method of claim 10, wherein said pharmaceutically acceptable salt is a hydrochloride.

12. The method of claim 10, wherein said compound is (–)-N-[[2-(8-methyl-1,4-benzodioxan-2-ylmethyl)amino] ethyl]tricyclo [3,3,1,1$^3$,$^7$] decane-1-carboxyamide.

* * * * *

UNITED STATES PATENT AND TRADEMARK OFFICE
CERTIFICATE OF CORRECTION

PATENT : 5,480,905

DATED : January 2, 1996

INVENTOR(S) : Akira Koda et al.

It is certified that error appears in the above-identified patent and that said Letters Patent is hereby corrected as shown below:

On the title page, item [63], "Continuation of Ser. No. 75,490, filed as PCT/JP92/01336, Oct. 21, 1992, abandoned." should read --Continuation of Ser. No. 75,490, filed June 21, 1993, abandoned, which was the national stage of international application number PCT/JP92/01366, filed Oct. 21, 1992.--.

Signed and Sealed this

Tenth Day of September, 1996

Attest:

BRUCE LEHMAN

*Attesting Officer*   *Commissioner of Patents and Trademarks*